US00PP15129P2

(12) United States Plant Patent
Gonzalez

(10) Patent No.: US PP15,129 P2
(45) Date of Patent: Aug. 31, 2004

(54) PORTULACA PLANT NAMED 'YUBI PRIMROSE'

(50) Latin Name: *Portulaca oleracea*
Varietal Denomination: Yubi Primrose

(75) Inventor: Javier Gonzalez, Salinas, CA (US)

(73) Assignee: Sakata Seed Corporation (JP)

( * ) Notice: Subject to any disclaimer, the term of this patent is extended or adjusted under 35 U.S.C. 154(b) by 0 days.

(21) Appl. No.: 10/374,910

(22) Filed: Feb. 25, 2003

(51) Int. Cl.[7] ..... A01H 5/00
(52) U.S. Cl. ..... Plt./263

(58) Field of Search ..... Plt./263

(56) References Cited

PUBLICATIONS

UPOV ROM GTITM Database GTI JOUVE Retrieval System 20032/05 Citation for 'Yubi Primrose'.*

* cited by examiner

*Primary Examiner*—Bruce R. Campell
*Assistant Examiner*—W C Haas
(74) *Attorney, Agent, or Firm*—Jondle & Associates P.C.

(57) ABSTRACT

Portulaca 'Yubi Primrose' is a new variety of *Portulaca oleracea*. This plant has a vigorous, spreading plant growth which produces a pale yellow flower.

1 Drawing Sheet

Genus and species: *Portulaca oleracea*.
Variety denomination: 'Yubi Primrose'.

BACKGROUND OF THE NEW PLANT

'Yubi Primrose' originated as a vegetative sport identified in 1999 in a greenhouse in Salinas, Calif., USA. This sport was found in the variety 'Summer Joy Pink'. The sport possessed pale yellow flowers. Unique flower color was the selection criteria at this stage of breeding.

ORIGIN AND ASEXUAL REPRODUCTION

Plants were propagated from vegetative cuttings using a peat moss-based mix. Cuttings formed roots in 7 to 10 days after sticking without the use of overhead mist. Rooted cuttings were transplanted into and in 15 cm diameter plastic pots in a glass greenhouse located in Salinas, Calif. Pots contained a peat moss-based growing medium. Soluble fertilizer containing 18% nitrogen, 8% phosphorus and 18% potassium was applied every fourth irrigation. The plants were typically watered twice a week. Pots were topdressed with a slow release fertilizer containing 18% nitrogen, 18% phosphorus and 8% potassium. The average air temperature was 24C.

After the initial propagation of the sport, five vegetative lines were made from the original plant in fall of 1999. In spring and summer of 2000 these lines were evaluated for uniformity and ease of propagation. One line was selected in fall 2000 and designated 'Yubi Primrose'. Uniformity of flower color and ease of propagation were the selection criteria. The following winter it was determined that the variety produced pinkish yellow flowers under low, winter light intensity. The variety has been observed for one more year and, other than the season color change, it has been determined that it is firmly fixed and stable.

BRIEF DESCRIPTION OF DRAWINGS

The accompanying drawings serve by color photographic means to illistrate the new plan variety. 'Yubi Primrose'. The colors are represented as true as possible using conventional photographic procedures.

DETAILED DESCRIPTION OF THE NEW VARIETY

Figure 1:
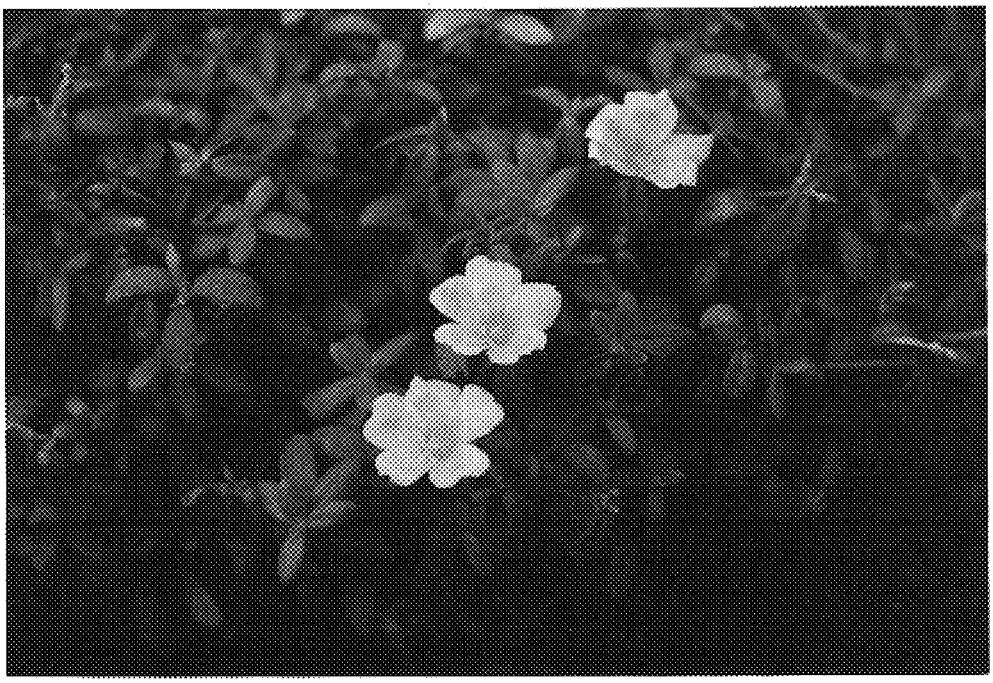
FIG. 1 is a close-up view of a 'Yubi Primrose' flower illustrating its color and shape.
Figure 2:
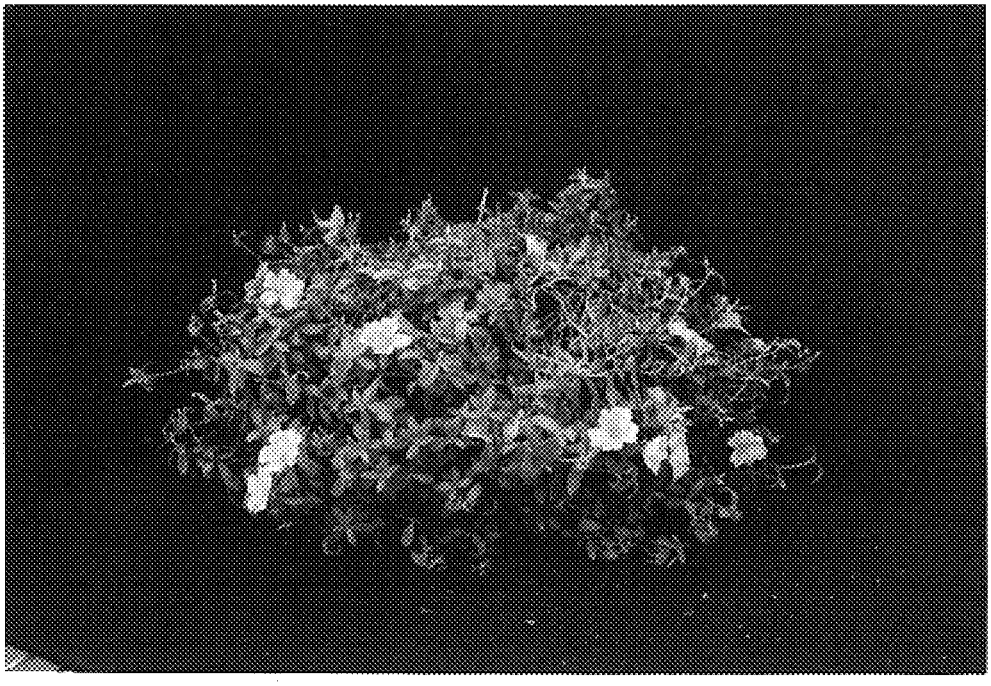
FIG. 2 is a view of the entire plant.

Color designations were made according to The Royal Horticultural Society Colour Chart published by The Royal Horticultural Society of London, England.

Origin: USA.
Parentage: Female parent — 'Summer Joy Pink' (U.S. Plant Pat. No. 12,277P2).
Classification:
- *Family.*—Portulacaceae.
- *Genus.*—Portulaca.
- *Species.*—*oleracea.*
- *Commercial.*—Portulaca/Purslane.

Plant:
- *Growth habit.*—Prostrate.
- *Plant height.*—23.0 cm.
- *Spread.*—85 cm.
- *Life cycle.*—Perennial.
- *Time to produce a rooted cutting.*—2 weeks.
- *Time to bloom from propagation.*—6–8 weeks.
- *Flowering season/requirements.*—Flowers year round at temperatures of 24°–35° C.; day neutral light requirements.
- *Temperature.*—Will not tolerate temperatures below 7° C.

Stem:
- *Color.*—RHS 144C (yellow-green).
- *Anthocyanin.*—RHS 178B (green-red).
- *Pubescence.*—Absent.
- *Stem description.*—Round, slightly round with lateral ridges.
- *Diameter.*—5.0 mm.
- *Length of internode.*—3.0–3.5 cm.

Leaf:

*Apex.*—Acute.
*Base.*—Rounded.
*Arrangement.*—Alternate.
*Leaf color.*—Upper surface RHS 137B (green); lower surface RHS 138A (green).
*Anthocyanin.*—RHS 178B (green-red).
*Margin.*—Entire.
*Length* (*average*).—2.5–3.0 cm.
*Width* (*average*).—1.2–1.5 cm.
*Shape.*—Oblong.
*Thickness.*—1.0 mm.
*Texture.*—Smooth.
*Petiole color.*—RHS N144D (yellow-green).
*Petiole length.*—2.0 mm.

Flower:

*Calyx.*—2 sepals; 1.0 cm×1.0 cm; free.
*Corolla.*—5 petals; free.
*Flower diameter.*—3.0–3.5 cm.
*Bud color.*—RHS 138B (green).
*Bud shape.*—Round and pointed at the top.
*Bud surface.*—Shiny.
*Duration of flower life.*—One day.
*Flowering habit.*—Indeterminate.
*Placenta arrangement.*—Central.
*Inflorescence type.*—Solitary, sessile.
*Stamens.*—Filament color RHS 150C (yellow-green); anther color RHS 25A (orange).
*Stigma.*—RHS 4B (yellow).
*Style.*—RHS 4B (yellow).
*Petal size.*—1.9–1.6 cm (l×w).
*Petal color.*—Upper surface RHS 4B (yellow) with RHS 60D (red-purple) surrounding the petal mid-vein; lower surface RHS 4B (yellow); base of petal absent.

DISEASE AND INSECT RESISTANCE

No unusual susceptibility to diseases or insects have been observed.

COMPARISON WITH OTHER KNOWN VARIETIES

'Yubi Primrose' is a distinct variety of Portulaca plant owing to its pale yellow petal color. 'Yubi Primrose' is most similar to the variety 'Summer Joy Yellow'. 'Yubi Primrose' possesses slightly smaller flowers than 'Summer Joy Yellow' and where 'Summer Joy Yellow' has golden yellow flowers, 'Yubi Primrose' possesses pale yellow flowers. Under low, winter light conditions (Northern Hemisphere) the petals of 'Yubi Primrose' possesses a red-purple blush around the mid-vein region.

We claim:

1. A new and distinct Portulaca plant, as shown and described herein.

* * * * *